United States Patent
Piron et al.

(10) Patent No.: US 10,307,181 B2
(45) Date of Patent: Jun. 4, 2019

(54) SYSTEM AND METHOD FOR GUIDED PORT INSERTION TO MINIMIZE TRAUMA

(71) Applicants: Cameron Anthony Piron, Toronto (CA); Michael Frank Gunter Wood, Toronto (CA); Murugathas Yuwaraj, Toronto (CA); Joshua Lee Richmond, Toronto (CA)

(72) Inventors: Cameron Anthony Piron, Toronto (CA); Michael Frank Gunter Wood, Toronto (CA); Murugathas Yuwaraj, Toronto (CA); Joshua Lee Richmond, Toronto (CA)

( * ) Notice: Subject to any disclaimer, the term of this patent is extended or adjusted under 35 U.S.C. 154(b) by 226 days.

(21) Appl. No.: 14/908,145

(22) PCT Filed: Mar. 12, 2015

(86) PCT No.: PCT/IB2015/051783
§ 371 (c)(1),
(2) Date: Jan. 28, 2016

(87) PCT Pub. No.: WO2016/142749
PCT Pub. Date: Sep. 15, 2016

(65) Prior Publication Data
US 2017/0042570 A1    Feb. 16, 2017

(51) Int. Cl.
*A61B 17/34* (2006.01)
*A61M 25/01* (2006.01)
(Continued)

(52) U.S. Cl.
CPC .......... *A61B 17/3403* (2013.01); *A61B 17/34* (2013.01); *A61B 17/3421* (2013.01);
(Continued)

(58) Field of Classification Search
CPC ................. A61B 17/3421; A61B 17/3476
(Continued)

(56) References Cited

U.S. PATENT DOCUMENTS 3,905,356 A * 9/1975 Fletcher ............... A61B 5/1107
338/2
4,449,532 A * 5/1984 Storz .................. A61B 1/00154
600/114
(Continued)

OTHER PUBLICATIONS

Young, Lee W., Examiner. International Search Report, PCT/IB2015/051783, dated Sep. 2, 2015.

*Primary Examiner* — Vy Q Bui

(57) ABSTRACT

The present invention provides a system and method for inserting a surgical port to minimize trauma. The system includes an access port and a guiding mechanism on the distal end of the access port, wherein the guiding mechanism has an adaptive atraumatic tip. The system also includes an introducer probe with a handle on the proximal end of the introducer probe, an atraumatic tip on the distal end of the introducer probe and a flexible body for insertion through the access port, the flexible body comprising one or more bendable elbows along the length of the introducer probe, wherein the introducer slidably engages the interior of the surgical access port to define an access path. The method includes inserting an access port down a sulcal path, inserting an introducer probe through the access port, and navigating the sulcal path with the introducer to the target.

21 Claims, 15 Drawing Sheets

(51) Int. Cl.
*A61B 90/11* (2016.01)
*A61B 17/00* (2006.01)
*A61B 17/32* (2006.01)
*A61B 34/30* (2016.01)
*A61B 90/00* (2016.01)

(52) U.S. Cl.
CPC .......... *A61B 17/3476* (2013.01); *A61B 90/11* (2016.02); *A61M 25/0113* (2013.01); *A61B 2017/00991* (2013.01); *A61B 2017/320048* (2013.01); *A61B 2017/3409* (2013.01); *A61B 2017/3443* (2013.01); *A61B 2017/3456* (2013.01); *A61B 2034/301* (2016.02); *A61B 2090/3735* (2016.02); *A61B 2090/3784* (2016.02)

(58) Field of Classification Search
USPC .............................................. 606/1, 130, 185
See application file for complete search history.

(56) References Cited

U.S. PATENT DOCUMENTS

| | | |
|---|---|---|
| 6,755,862 B2 * | 6/2004 | Keynan .................. A61B 17/72 606/170 |
| 2010/0010315 A1 | 1/2010 | Mangiardi |
| 2011/0054260 A1 * | 3/2011 | Albrecht ............ A61B 17/0218 600/208 |
| 2011/0230894 A1 | 9/2011 | Simaan et al. |
| 2012/0209077 A1 * | 8/2012 | Racenet ............. A61B 17/3423 600/206 |
| 2013/0072856 A1 * | 3/2013 | Frankhouser ........ A61B 10/025 604/22 |
| 2013/0102851 A1 | 4/2013 | Mark et al. |
| 2014/0343364 A1 * | 11/2014 | Albrecht ............ A61B 17/0293 600/204 |
| 2016/0213434 A1 * | 7/2016 | Lohmeier .............. A61B 34/30 |

* cited by examiner

SYSTEM AND METHOD FOR GUIDED PORT INSERTION TO MINIMIZE TRAUMA

FIELD

The present disclosure relates to navigation systems and methods for minimally invasive therapy and image guided medical procedures.

BACKGROUND

The present disclosure is generally related to image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, mechanical stress to the brain matter, unintentional impact with surgical devices, and/or accidental resection of healthy tissue.

Thus, there is a need for mechanisms to define an appropriate access port path, to minimize trauma when navigating down the path.

Probes for optical measurements of tissue are being developed for a wide variety of applications and modalities, all focused on providing clinicians with details regarding the state of tissue to guide diagnosis or treatments. While the low penetration of light into biological tissue (on the order of 2 mm) restricts the use of optical techniques to surface or near surface measurements, the potential for optical probes to be miniaturized opens the possibility for probes to be combined with endoscopic or catheter-based techniques. This allows for optical measurements to be made in a wide variety of hollow organs (esophagus, colon, lung, etc.) and as a part of many minimally invasive surgical techniques. The optical modalities for which probes have been developed include broadband spectroscopy (ultraviolet, visible, near infrared, and short wave infrared), fluorescence, Raman spectroscopy, optical coherence tomography, photoaccoustic tomography, coherence anti-Stokes Raman spectroscopy, confocal microscopy, among others.

Port-based or corridor surgery is a minimally invasive surgical technique where a port (generally a cylindrical plastic tube open on both ends) is introduced to access the surgical region of interest. Unlike other minimally invasive techniques, such as laparoscopic techniques, the port diameter is larger than the tool diameter, allowing bi-manual tool manipulation within the port. Hence, the tissue region of interest is accessible through the port. The presence of the tissue region of interest at a depth of a few centimeters below the skin surface and accessible through a narrow corridor allows for optical probe measurements to be made on regions of interest in close proximity to the tissue (contact probe within the port) and at a standoff distance from the tissue (stand-off probe position outside of the port).

While a wide variety of optical probes have been developed for numerous modalities, specific design aspects to enable and enhance the use of these probes within port-based surgery have not been developed. These include: the size of the probe, sterilization tolerance, signal enhancing mechanisms, integration with surgical tools, position and orientation tracking, and integration with other optical systems. At present the lack of these features hinders and restricts the use and utility of probes for port-based surgery.

Thus there is a need to develop probes with design aspects that may enable and enhance their use within port-based surgery.

SUMMARY

A further understanding of the functional and advantageous aspects of the disclosure can be realized by reference to the following detailed description and drawings.

An object of the invention is to provide a system and method for guided port insertion to minimize trauma.

Thus by one broad aspect of the present invention, the invention provides a surgical access port for navigating down a sulcal path of a neurosurgical procedure comprising a cylindrical body having a proximal end and a distal end, and a guiding mechanism on the distal end of the access port wherein the guiding mechanism has an adaptive atraumatic tip.

By another broad aspect of the present invention, the invention provides an introducer probe for use with a surgical access port in a neurosurgical procedure comprising a handle on the proximal end of the introducer probe, an atraumatic tip on the distal end of the introducer probe, and a flexible body for insertion through the access port, the flexible body comprising one or more bendable elbows along the length of the introducer probe, wherein the introducer slidably engages the interior of the surgical access port to define an access path.

By another broad aspect of the present invention, a method is provided for navigating down a sulcal path to a target in a surgical procedure comprising the steps of inserting an access port down a sulcal path, inserting an introducer probe through the access port, and navigating the sulcal path with the introducer to the target.

BRIEF DESCRIPTION OF THE DRAWINGS

Embodiments will now be described, by way of example only, with reference to the drawings, in which.

DETAILED DESCRIPTION

Figure 1:
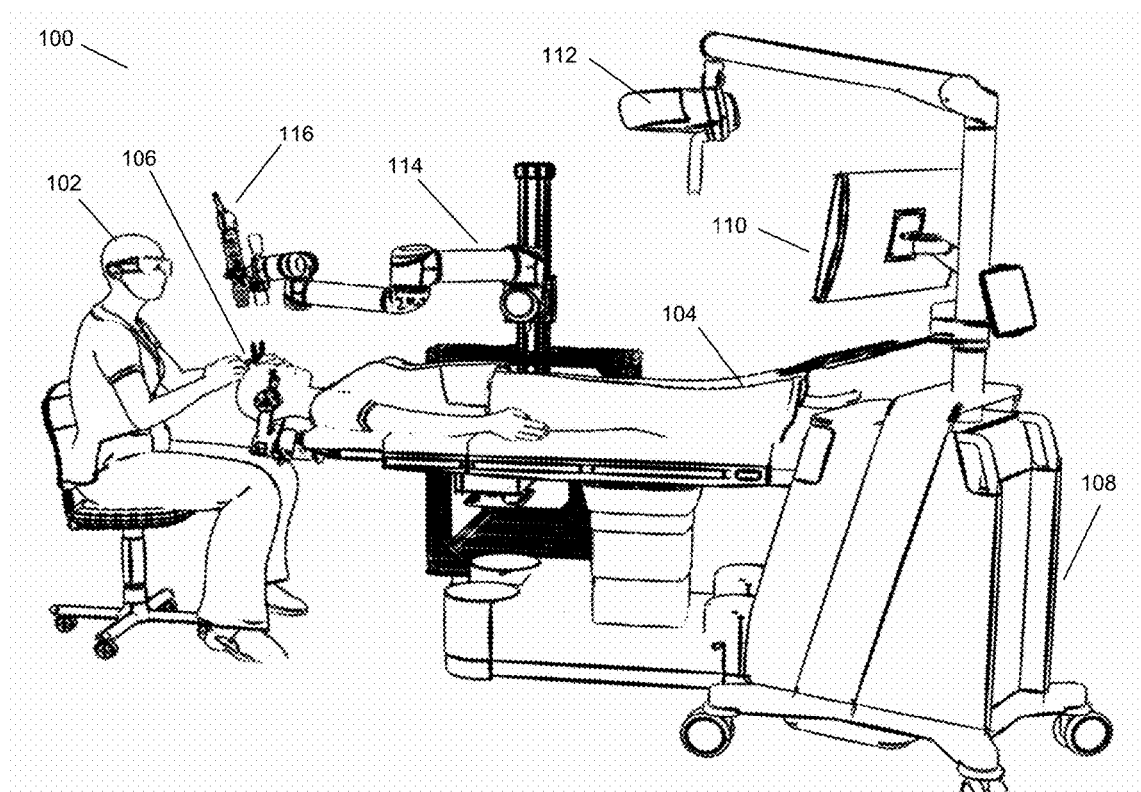
FIG. 1 depicts an operating theatre, according to a non-limiting embodiment.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. The access port can include a sheath (the port that is left behind to access surgical area) and an obturator (introducer). In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

An example of an access port is an intracranial access port which may be employed in neurological procedures in order to provide access to internal tissue pathologies, such as tumors. One example of an intracranial access port is the BrainPath surgical access port provided by NICO, which may be inserted into the brain via an obturator with an atraumatic tip in the brain. Such an access port may be employed during a surgical procedure, by inserting the access port, via the obturator that is received within the access port, through the white matter fibers of the brain to access a surgical site.

FIG. 1 depicts a surgical operating theatre 100 in which a healthcare worker 102 (e.g. a surgeon) operates on a patient 104. Specifically, surgeon 102 is shown conducting a minimally invasive surgical procedure on the brain of patient 104. Minimally invasive brain surgery involves the insertion and manipulation of instruments into the brain through an opening that is significantly smaller than the portions of skull removed to expose the brain in traditional brain surgery techniques. The description below makes reference to the brain of patient 104 as an example of tissue to which the techniques herein may be applied. It will be understood, however, that those techniques may also be applied to a wide variety of other tissues. Thus, when the brain of patient 104 is mentioned below, it is simply an example of the various tissues in connection with which the systems and methods herein may be implemented.

The opening through which surgeon 102 inserts and manipulates instruments is provided by an access port 106. Access port 106 typically includes a hollow cylindrical device with open ends. During insertion of access port 106 into the brain (after a suitable opening has been drilled in the skull), an introducer, also referred to as an obturator (not shown) is generally inserted into access port 106. The introducer is typically a cylindrical device that slidably engages the internal surface of access port 106 and bears a conical atraumatic tip to allow for insertion of access port 106 into the brain. Following insertion of access port 106, the introducer may be removed, and access port 106 may then enable insertion and bimanual manipulation of surgical tools into the brain. Examples of such tools include suctioning devices, scissors, scalpels, cutting devices, imaging devices (e.g. ultrasound sensors) and the like.

Also shown in FIG. 1 is an equipment tower 108 supporting a computing device (not shown) such as a desktop computer, as well as one or more displays 110 connected to the computing device for displaying images provided by the computing device.

Equipment tower 108 also supports a tracking system 112. Tracking system 112 is generally configured to track the positions of one or more reflective markers (not shown) mounted on access port 106, any of the above-mentioned surgical tools, or any combination thereof. Such markers, also referred to as fiducial markers, may also be mounted on patient 104, for example at various points on the head of patient 104. Tracking system 112 may therefore include a camera (e.g. a stereo camera) and a computing device (either the same device as mentioned above or a separate device) configured to locate the fiducial markers in the images captured by the camera, and determine the spatial positions of those markers within the operating theatre. The spatial positions may be provided by tracking system 112 to the computing device in equipment tower 108 for subsequent use.

The nature of the markers and the camera are not particularly limited. For example, the camera may be sensitive to infrared (IR) light, and tracking system 112 may include one or more IR emitters (e.g. IR light emitting diodes (LEDs)) to shine IR light on the markers. In other examples, marker recognition in tracking system 112 may be based on radio frequency (RF) radiation, visible light emitted from devices such as pulsed or un-pulsed LEDs, electromagnetic radiation other than IR or visible light, and the like. For RF and EM-based tracking, each object can be fitted with markers having signatures unique to that object, and tracking system 112 can include antennae rather than the above-mentioned camera. Combinations of the above may also be employed.

Each tracked object generally includes three or more markers fixed at predefined locations on the object. The predefined locations, as well as the geometry of each tracked object, are configured within tracking system 112, and thus tracking system 112 is configured to image the operating theatre, compare the positions of any visible markers to the pre-configured geometry and marker locations, and based on the comparison, determine which tracked objects are present in the field of view of the camera, as well as what positions those objects are currently in. An example of tracking system 112 is the "Polaris" system available from Northern Digital Inc.

Also shown in FIG. 1 is an automated articulated arm 114, also referred to as a robotic arm, carrying an external scope 116 (i.e. external to patient 104). External scope 116 may be positioned over access port 106 by robotic arm 114, and may capture images of the brain of patient 104 for presentation on display 110. The movement of robotic arm 114 to place external scope 116 correctly over access port 106 may be guided by tracking system 112 and the computing device in equipment tower 108. The images from external scope 116 presented on display 110 may be overlaid with other images, including images obtained prior to the surgical procedure. The images presented on display 110 may also display virtual models of surgical instruments present in the field of view of tracking system 112 (the positions and orientations of the models having been determined by tracking system 112 from the positions of the markers mentioned above).

Before a procedure such as that shown in FIG. 1 (which may be, for example, a tumor resection), preoperative images may be collected of patient 104, or at least of the brain of patient 104 or portions thereof. Such preoperative images may be collected using any of a variety of imaging modalities, such as Magnetic Resonance Imaging (MRI), Optical Coherence Tomography (OCT), ultrasound, Computed Tomography (CT), optical spectroscopy and the like. For each of the above-mentioned imaging modalities, various imaging techniques may be used. Polarization Sensitive OCT and OCT elastography are exemplary uses of the OCT modality. Diffusion MRI (also referred to as diffusion tensor imaging, DTI) is an example use of the MRI modality. Raman spectroscopy is an example use of optical spectroscopy. A variety of other examples of the above modalities will also occur to those skilled in the art.

Preoperative images may be used for planning purposes. Examples of planning activities include marking, in the preoperative images, the location of a target portion of patient tissue. Such a target portion may include a tumor to be resected, for example. During the procedure, additional images (referred to as intraoperative images) may be collected of the brain of patient 104 using any suitable one of the above-mentioned modalities (it will be apparent to those skilled in the art that some imaging modalities are less suitable or unsuitable for preoperative use, while other imaging modalities are less suitable or unsuitable for intraoperative use). In addition, as will be discussed below in greater detail, further images may be acquired during the procedure (or after the procedure has concluded) of tissue samples resected from patient 104.

As will be described in further detail below, the computing device housed in equipment tower 108 can perform various actions to employ the above-mentioned preoperative images and intraoperative images to automatically evaluate the accuracy of a resection procedure, in comparison with the planned resection.

Figure 2:
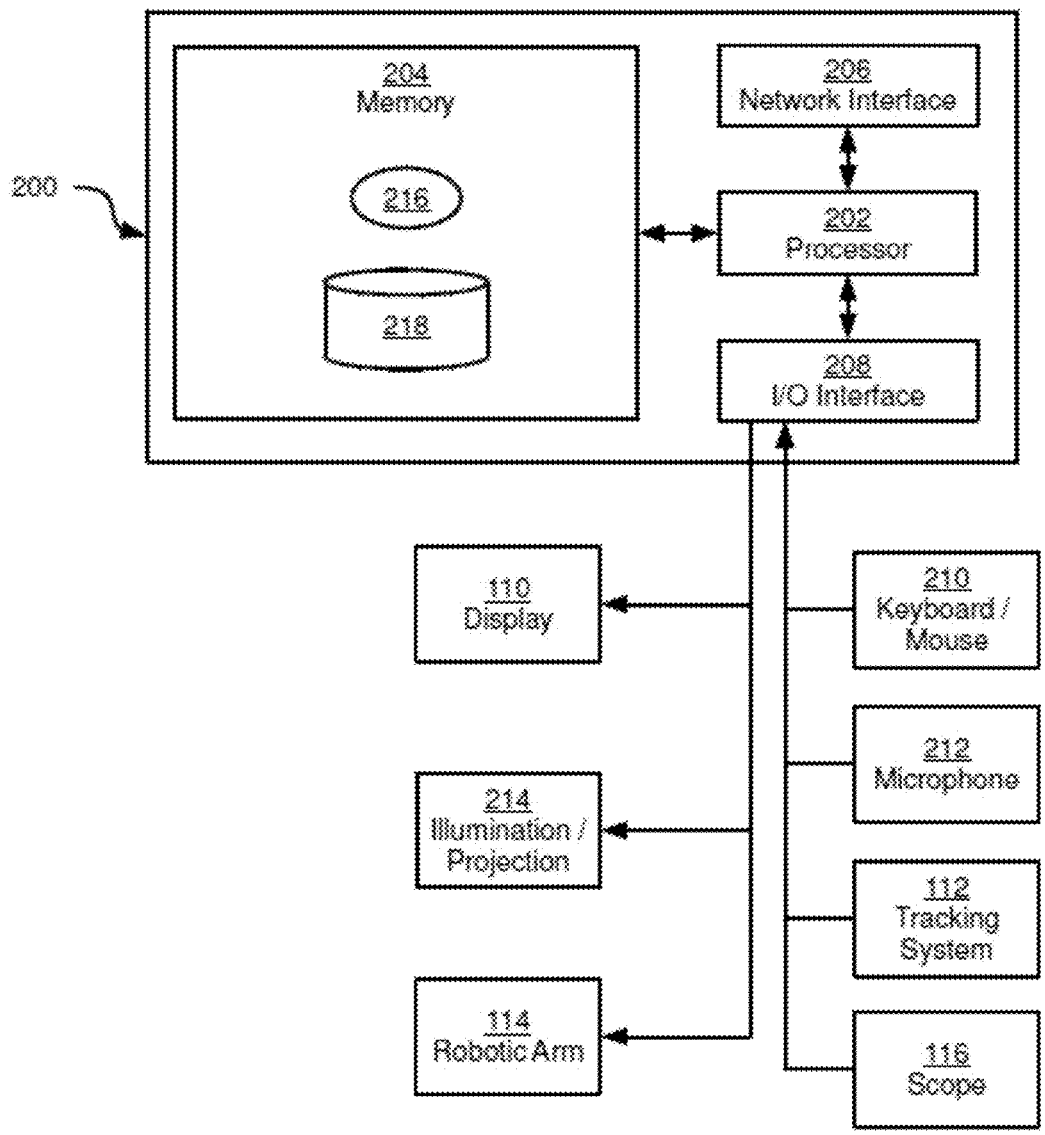
FIG. 2 depicts a computing device of the operating theatre of FIG. 1, according to a non-limiting embodiment.

Before a discussion of the functionality of the computing device, a brief description of the components of the computing device will be provided. Referring to FIG. 2, a computing device 200 is depicted, including a central processing unit (also referred to as a microprocessor or simply a processor) 202 interconnected with a non-transitory computer readable storage medium such as a memory 204.

Processor 202 and memory 204 are generally comprised of one or more integrated circuits (ICs), and can have a variety of structures, as will now occur to those skilled in the art (for example, more than one CPU can be provided). Memory 204 can be any suitable combination of volatile (e.g. Random Access Memory ("RAM")) and non-volatile (e.g. read only memory ("ROM"), Electrically Erasable Programmable Read Only Memory ("EEPROM"), flash memory, magnetic computer storage device, or optical disc) memory. In the present example, memory 204 includes both a volatile memory and a non-volatile memory. Other types of non-transitory computer readable storage medium are also contemplated, such as compact discs (CD-ROM, CD-RW) and digital video discs (DVD).

Computing device 200 also includes a network interface 206 interconnected with processor 202. Network interface 206 allows computing device 200 to communicate with other computing devices via a network (e.g. a local area network (LAN), a wide area network (WAN) or any suitable combination thereof). Network interface 206 thus includes any necessary hardware for communicating over such networks, such as radios, network interface controllers (NICs) and the like.

Computing device 200 also includes an input/output interface 208, including the necessary hardware for interconnecting processor 202 with various input and output devices. Interface 208 can include, among other components, a Universal Serial Bus (USB) port, an audio port for sending and receiving audio data, a Video Graphics Array (VGA), Digital Visual Interface (DVI) or other port for sending and receiving display data, and any other suitable components.

Via interface 208, computing device 200 is connected to input devices including a keyboard and mouse 210, a microphone 212, as well as scope 116 and tracking system 112, mentioned above. Also via interface 208, computing device 200 is connected to output devices including illumination or projection components 214 (e.g. lights, projectors and the like), as well as display 110 and robotic arm 114 mentioned above. Other input (e.g. touch screens) and output devices (e.g. speakers) will also occur to those skilled in the art.

It is contemplated that I/O interface 208 may be omitted entirely in some embodiments, or may be used to connect to only a subset of the devices mentioned above. The remaining devices may be connected to computing device 200 via network interface 206.

Computing device 200 stores, in memory 204, a resection evaluation application 216 (also referred to herein as application 216) comprising a plurality of computer readable instructions executable by processor 202. When processor 202 executes the instructions of application 216 (or, indeed, any other application stored in memory 204), processor 202 performs various functions implemented by those instructions, as will be discussed below. Processor 202, or computing device 200 more generally, is therefore said to be "configured" or "operating" to perform those functions via the execution of application 216.

Also stored in memory 204 are various data repositories, including a patient data repository 218. Patient data repository can contain surgical planning data, preoperative and intraoperative images, and the like, as will be seen below. As mentioned above, computing device 200 is configured, via the execution of application 216 by processor 202, to perform various functions to evaluate the accuracy of a resection procedure in order to confirm whether the planned target portion of the brain of patient 104 (or other tissue volume) was actually resected during the procedure. Those functions will be described in further detail below.

Further contents of this disclosure will be provided in two sections: "Mechanisms to Define a Port Path" and "Mechanisms to Drive a Port Down a Path".

1. Mechanisms to Define a Port Path

Steerable Probe

Figure 3:
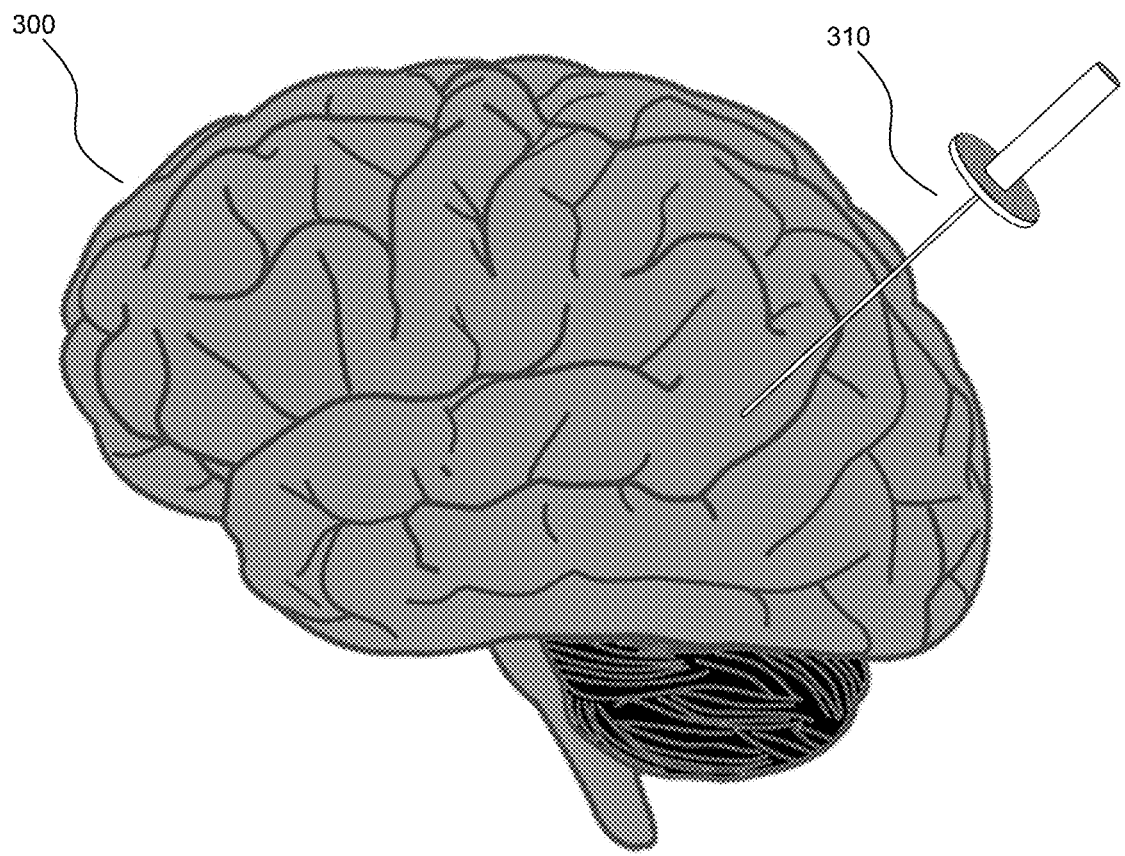
FIG. 3 illustrates the insertion of an access port into a human brain, for providing access to internal brain tissue during a medical procedure.

FIG. 3 illustrates the insertion of an access port into a human brain for providing access to internal brain tissue during a medical procedure. In FIG. 3, an access port 310 is inserted into a human brain 300, providing access to internal brain tissue. Surgical tools and instruments may then be inserted within the lumen of the access port in order to perform surgical, diagnostic or therapeutic procedures, such as resecting tumors as necessary.

During port-based or corridor based surgery, a straight (linear) access port 310 is typically guided down a sulci path of the brain. However, sulci paths of the brain are typically non-linear and may deviate/curve in multiple directions which makes it challenging to navigate to the target internal brain tissue.

Figure 4:
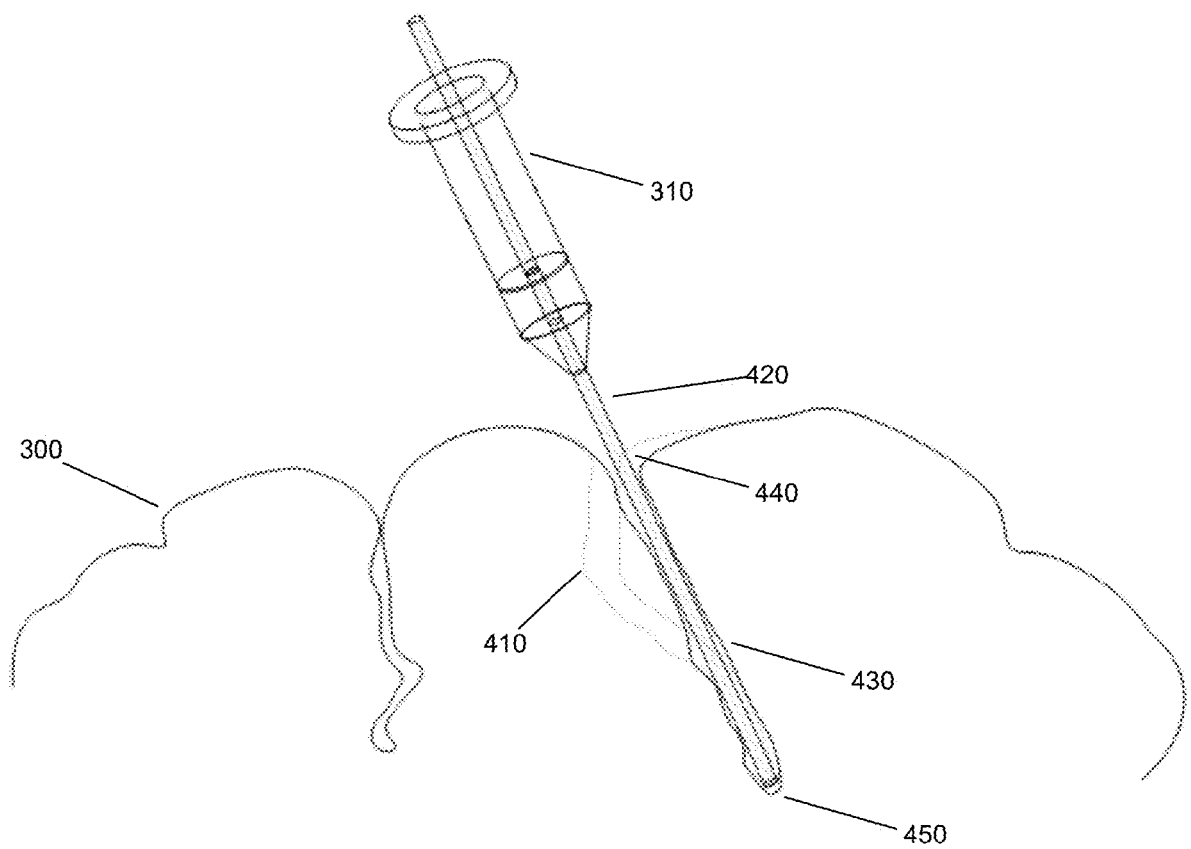
FIG. 4 illustrates the insertion of an access port and probe down a sulci path.

FIG. 4 illustrates an existing method of insertion of an access port and probe down a sulci path 410. In FIG. 4, access port 310 is positioned to navigate a human brain 300. Positioned within access port 310 is a linear (straight) probe 420. Probe 420 may be a resection tool, an image sensor and/or other types of sensing tools that can take measurements in different imaging modalities (e.g., ultrasound, Raman, OCT, PET, MRI, etc.).

Probe 420 enters the brain 300 at sulci entry opening 440 to navigate to targeted internal tissue 450. Ideally, probe 420 should follow sulci path 410, however, due to the linear and rigid nature of probe 420, a linear path 430 to targeted internal tissue 450 is mapped out. The linear and rigid nature of the probe may result in trauma to the brain matter due to stress or shear of the tissue.

Figure 5:
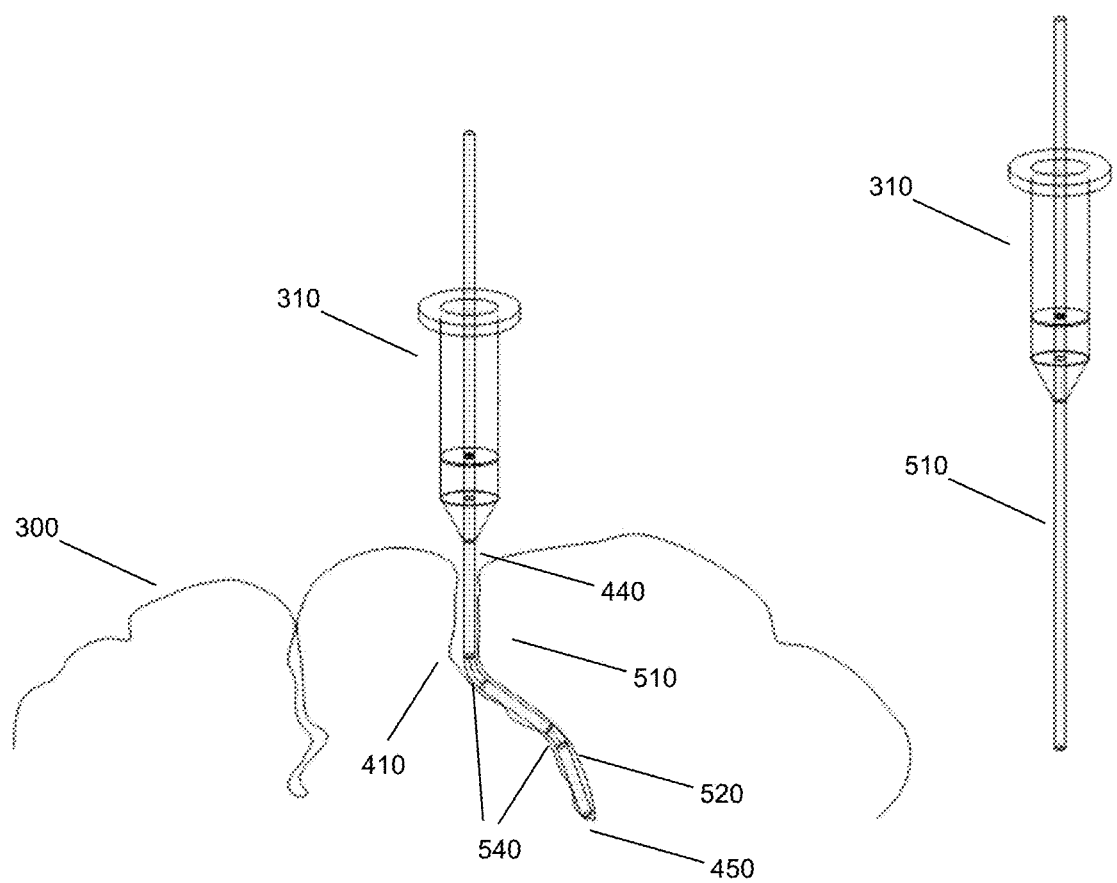
FIG. 5 illustrates the insertion of an access port down a sulci path using a flexible probe.

FIG. 5 illustrates an exemplary embodiment of access port insertion down a sulci path using a flexible probe. In FIG. 5, access port 310 is positioned to navigate a sulci path 410 of the human brain 300 to a targeted internal tissue 450. Positioned within access port 310 is a flexible probe 510. Flexible probe 510 comprises of one or more bendable elbows 540 that enables flexible probe 510 to bend to the contour/curvature of sulci path 410.

Flexible probe 510 enters the brain 300 at sulci entry opening 440 and would like to navigate to targeted internal tissue 450. Because of bendable elbows 540, flexible probe 510 may twist/turn into multiple directions to create an optimal path 520 to reach targeted internal tissue 450.

Figure 6A:
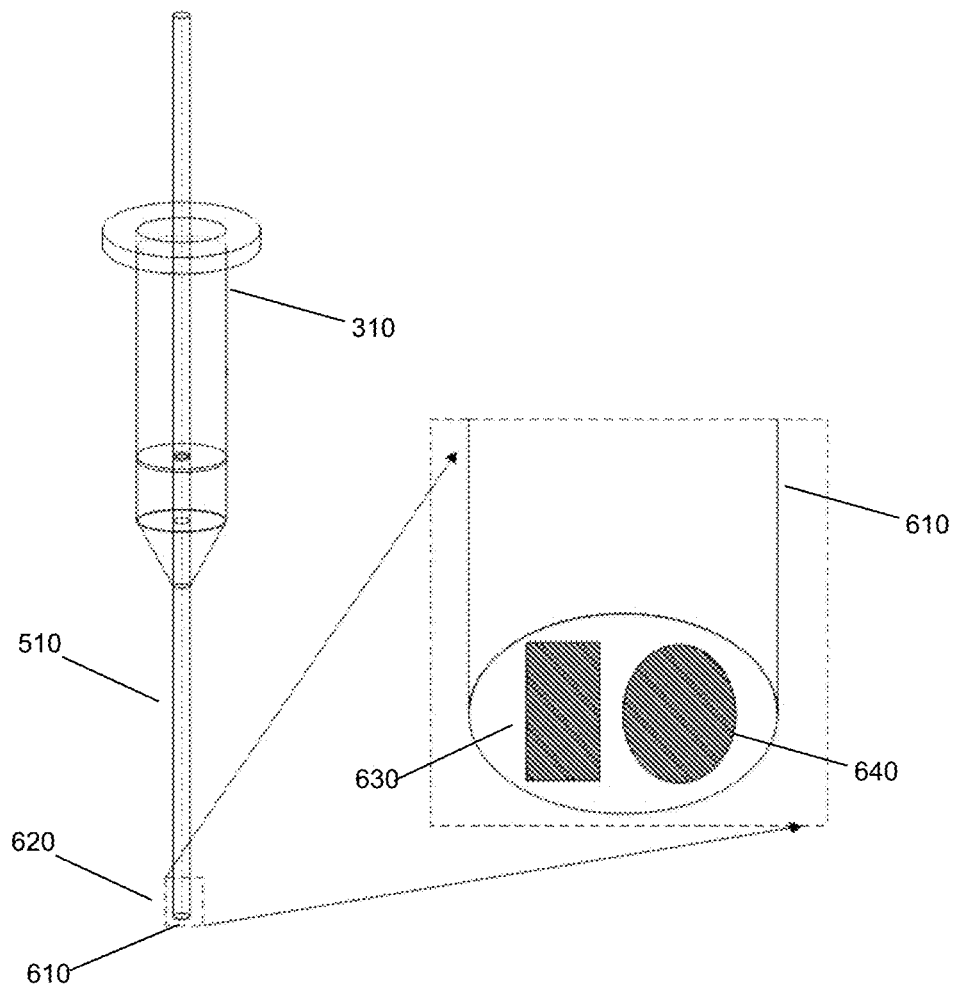
FIG. 6A illustrates a flexible probe having imaging sensors at the distal end.

FIG. 6A illustrates a flexible probe having imaging sensors at the distal end. The distal end 610 of flexible probe 510 may house different imaging sensors 620 and/or other types of sensing tools that can take measurements in different imaging modalities. As seen in FIG. 6A, imaging sensors 620 for ultrasound 630 and optical coherence tomography (OCT) 640 may be placed at distal end 610 of flexible probe 510. Other types of sensing tools such as fiber optics, light guides, Raman, PET, and MRI can also be considered as imaging sensors 620 that can be placed on flexible probe 510.

In the preferred embodiment shown in FIG. 6A, imaging sensors 620 are placed at the distal end 610 of flexible probe 510. In alternate embodiments, imaging sensors 620 may be placed in other locations such as along the length or proximal end of flexible probe 510, and/or along the length of the access port 310. In a further embodiment, the distal end 610 or tip of flexible probe 510 may also be retrofitted with a puncher/punching mechanism to punch through the dura, brain tissue or sulci path in order to navigate to the desired target.

As seen in FIG. 5 and FIG. 6A, the combination of bendable elbows 540 and imaging sensors 620 enables flexible probe 510 to be steerable, thus defining the path of the port that can more closely follow the sulci path 410. Navigation and control of bendable elbow 540 may be controlled by a user (i.e., surgeon or operator) or robotic arm where feedback can be provided by imaging sensor 620 on flexible probe 510 or other sensing tools nearby. Bendable elbow 540 may also be locked in place to create a lock path when in use and can also be straightened to return flexible probe 510 back to its original linear position.

Figure 6B:
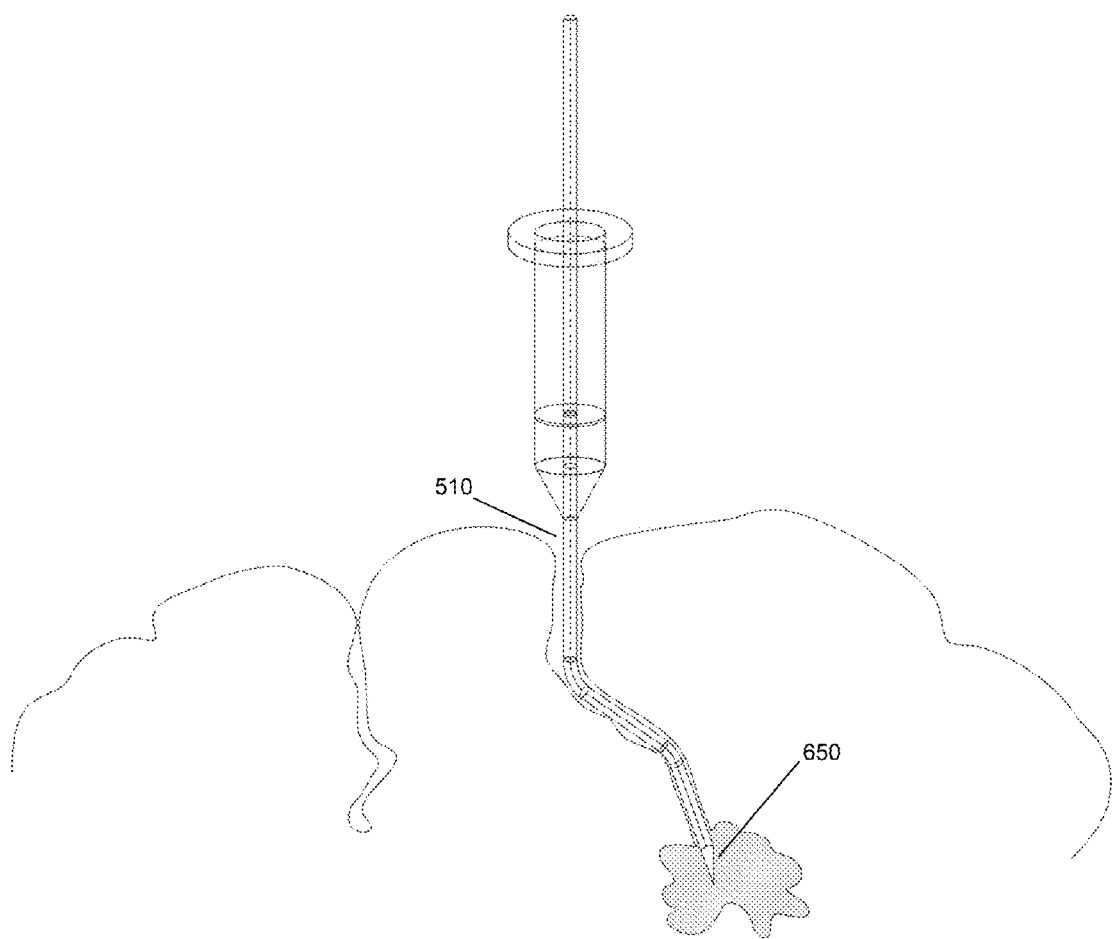
FIG. 6B illustrates a flexible probe having a biopsy extraction tool.

In addition to supporting imaging sensors 620, the distal end 610 of flexible probe 510 may also be equipped with alternate tools. In FIG. 6B, flexible probe 510 is equipped with a biopsy extraction tool 650. The biopsy extraction tool 650 can be used to remove a tissue specimen at the distal end 610 of flexible probe 510. The tissue specimen may be collected in a biopsy chamber external to the patient via a biopsy tube connecting the biopsy extraction tool 650 and the biopsy chamber. The tissue specimen may be evaluated during surgery, for example by gross examination or by cryosectioning, staining and observing the tissue specimen microscopically. Biopsy evaluation during surgery provides real-time diagnosis of the tissue located at the distal end of the flexible probe, and may inform whether the biopsied tissue is tumor or normal, and whether tumor tissue is benign or malignant. Intraoperative biopsy evaluation can be used to determine further surgical options, such as whether to continue with tissue resection. Intraoperative tissue evaluation may also be used to validate that the distal end 610 of the flexible probe 510 is correctly positioned at the tumor site.

Figure 6C:
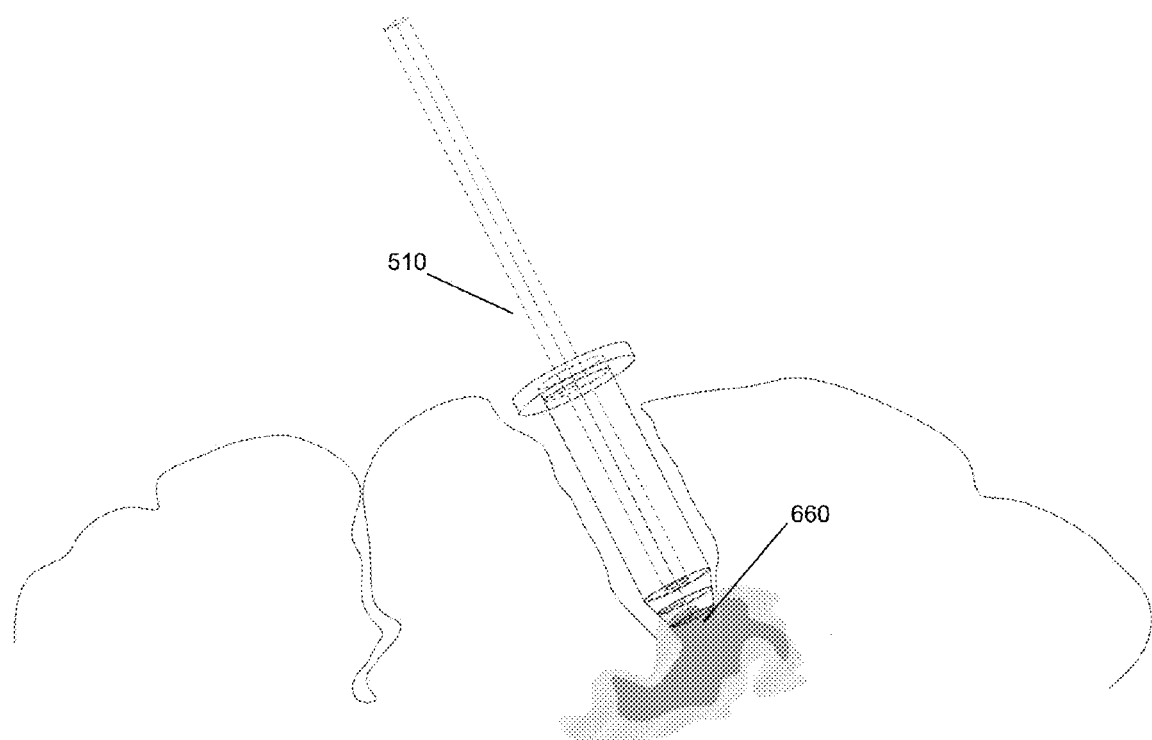
FIG. 6C illustrates a flexible probe having fluorescence markers.

In an alternate embodiment as seen in FIG. 6C, the distal end of flexible probe 510 may also be equipped with a dye tool 660. The dye tool 660 enables tissue staining at the distal end of the flexible probe 510 for subsequent location reference. For example, the dye tool 660 may provide a location reference for the location of a biopsy taken using the biopsy extraction tool 650. The dye tool 660 can deposit an intravital stain or fluorescent marker, such as methylene blue or fluorescein. The dye tool may also be used to dispense MR contrast agent, which can be used subsequently for MRI imaging of the patient to verify the location of the biopsy, resection or tumor.

2. Mechanisms for Driving Port Down to Target

Once an access port path has been defined, the next step is to insert the access port down the desired path to the target tissue (i.e., cancerous tissue to be resected). Insertion of the access port can be obstructed by the brain structures and forceful insertion may result in trauma, thus it is desirable to pursue various port insertion mechanisms that may minimize trauma.

Inflatable Balloon

Figure 7A:
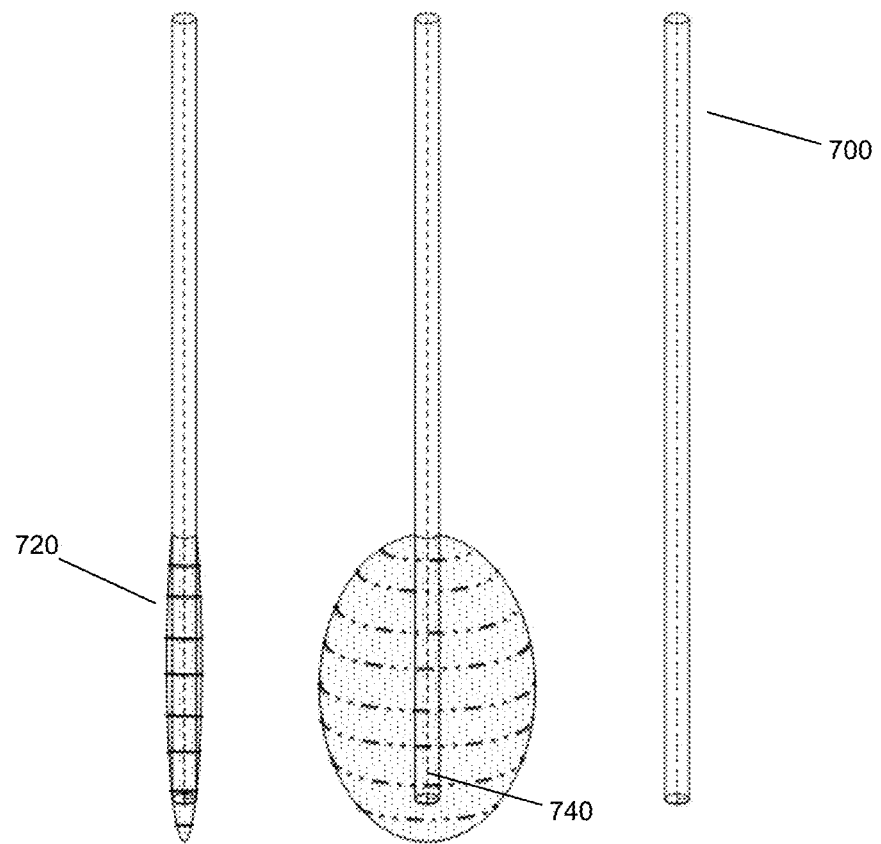
FIG. 7A illustrates an example of an inflatable balloon probe.

One port insertion mechanism is an inflatable balloon probe. FIG. 7A illustrates an inflatable balloon probe. Inflatable probe 700 comprises a sealed balloon structure 720 attached to the distal end of inflatable probe 700. Air holes 740 on inflatable probe 700 enable sealed balloon 720 to be inflated once air or pressure is applied. FIG. 7A illustrates the three states of balloon 720. Balloon 720 is uninflated in the right image, partially inflated in the left image and fully inflated in the center image. Once the balloon 720 is partially or fully inflated, balloon 720 applies pressure within the tissue to displace brain tissue fibers and allow insertion of the port.

Figure 7B:
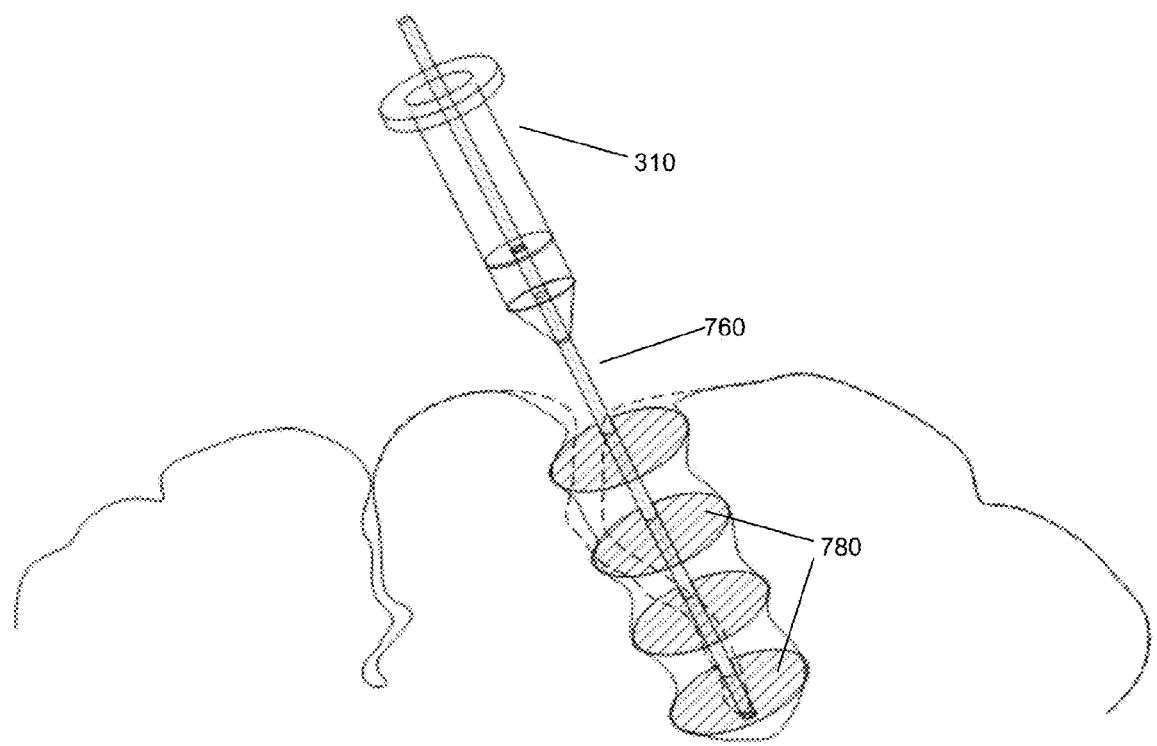
FIG. 7B illustrates an example of multiple inflatable balloons probe.

FIG. 7B illustrates a further embodiment illustrating the concept of a probe with multiple inflatable balloons. In FIG. 7B, probe 760 is inserted into access port 310. Probe 760 comprises multiple inflatable balloons 780. When air pressure is applied, balloons 780 will inflate to a desired diameter which will expand the desired sulci path making it easier for port 310 to be inserted down the desired path with the intention of reducing trauma.

In an alternate embodiment, inflatable balloons may be placed on the outer walls of the access port where the balloons can be inflated. This enables a small port to be inserted whose diameter can be increased once inserted to allow for a larger operating channel.

High Frequency Vibration

Figure 8:
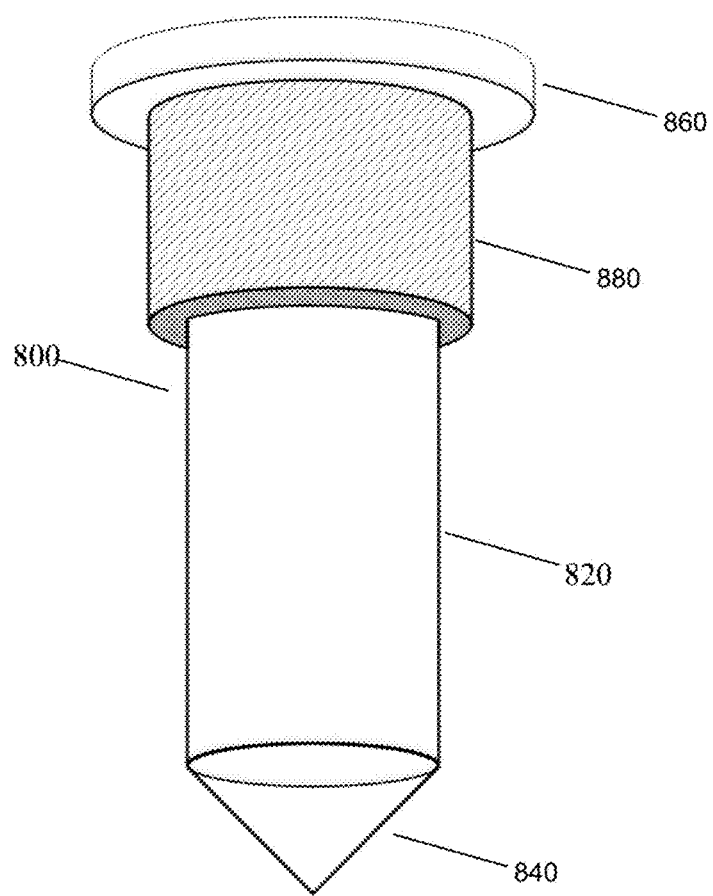
FIG. 8 illustrates an example of a port with a high frequency obturator.

A second mechanism to assist in access port insertion is to use high frequency vibration to reduce friction as an access port is inserted down a path. FIG. 8 illustrates an access port with a high frequency vibration mechanism. In FIG. 8, access port 800 comprises a cylindrical barrel 820, an atraumatic tip 840 at the distal end of the cylindrical barrel, and a rim 860 at the proximal end of the cylindrical barrel. Rim 860 typically protrudes outside of the brain tissue after insertion of the access port 800. Atraumatic tip 840 is preferably conical in shape with a tip point. Housed along the cylindrical barrel 820 is vibration source 880 that is mechanically coupled to the exterior surface of the cylindrical barrel. The vibration source 880 may be an ultrasonic transducer fashioned in the shape of a cylinder.

Vibration source 880 uses high frequency vibrations, typically working in the ultrasonic range of 20 KHz-1 MHz, to reduce the friction caused by the insertion of the access port 800. In a further embodiment, vibrating obturator 880 may vibrate in resonance to increase efficiency and power transfer. Vibration source 880 may be enabled by a surgeon or robotic surgical system and may be adjustable in frequency and amplitude. An example of an ultrasonic vibration mechanism may be a piezo-electric transducer that is actuated by electrical pulses. Vibration source 880 may comprise a driver circuit, amplifier, oscillator and a power supply.

The access port 800 and vibration source 880 may be made of biocompatible material such as inert polymers (Kevlar, liquid crystal polymer). Alternatively, the mechanism may be made of sterilizable material such as stainless steel. The cylindrical barrel 820 may further be coated with a low-friction coating.

Adaptive Tip

A further mechanism to ease port insertion is provided by an access port with an introducer (also referred to as an obturator) that bears an adaptive atraumatic tip, wherein the tip configuration may be changed depending on the context or stage of surgery. The introducer is typically a cylindrical device that slidably engages the internal surface of a port and bears an atraumatic tip.

Figure 9A:
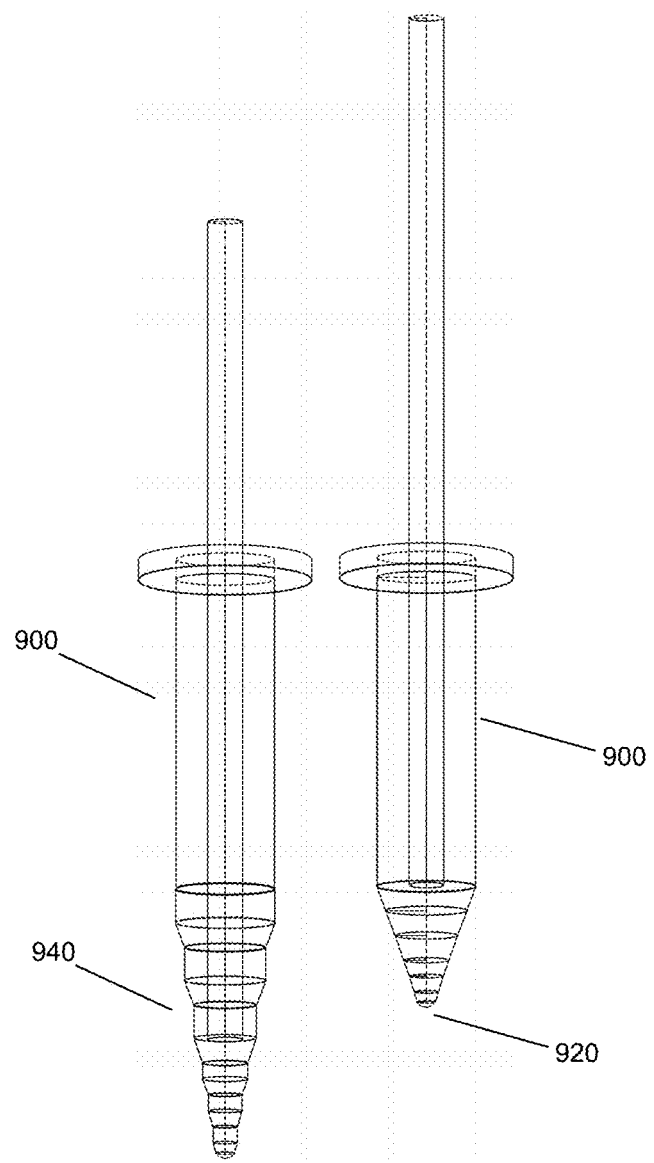
FIG. 9A illustrates an example of a port with an adaptive tip.

FIG. 9A illustrates an example of an access port with an adaptive atraumatic tip shown in both a collapsed and extended position. Access port 900, having an atraumatic tip 920 on its distal end, is shown in a collapsed position on the right image of FIG. 9A. In a preferred embodiment, atraumatic tip 920 is conical in shape and is constructed of a plurality of concentric rings 940. Concentric rings 940 can expand to an extended position, as shown in the left image of FIG. 9A, forming a longer atraumatic tip 920.

The atraumatic tip 920 may be considered as a "collapsible salad bowl" concept wherein the atraumatic tip can be collapsed and expanded based on use. The atraumatic tip 920 may have either a mechanical or electrical drive that can be controlled by a linear drive motor to pull up (collapse) or push down (extend) the atraumatic tip.

In a preferred embodiment, the atraumatic tip 920 includes a series of rigid concentric rings with successively smaller diameters, thus providing a conical shape. In a further preferred embodiment, the concentric rings are shaped as truncated cones with decreasing base diameter. Each concentric ring may be connected to the adjacent concentric ring with a flexible membrane, such as surgical-grade silicone. The flexible membrane may include "living hinges" in the membrane perimeter abutting the concentric rings, which are more likely than the rest of the membrane to fold under force and cause the membrane to fold inward when the atraumatic tip is in the collapsed position. The flexible membrane further helps maintain a waterproof barrier between the tissue that is being penetrated and the introducer or obturator.

Figure 9B:
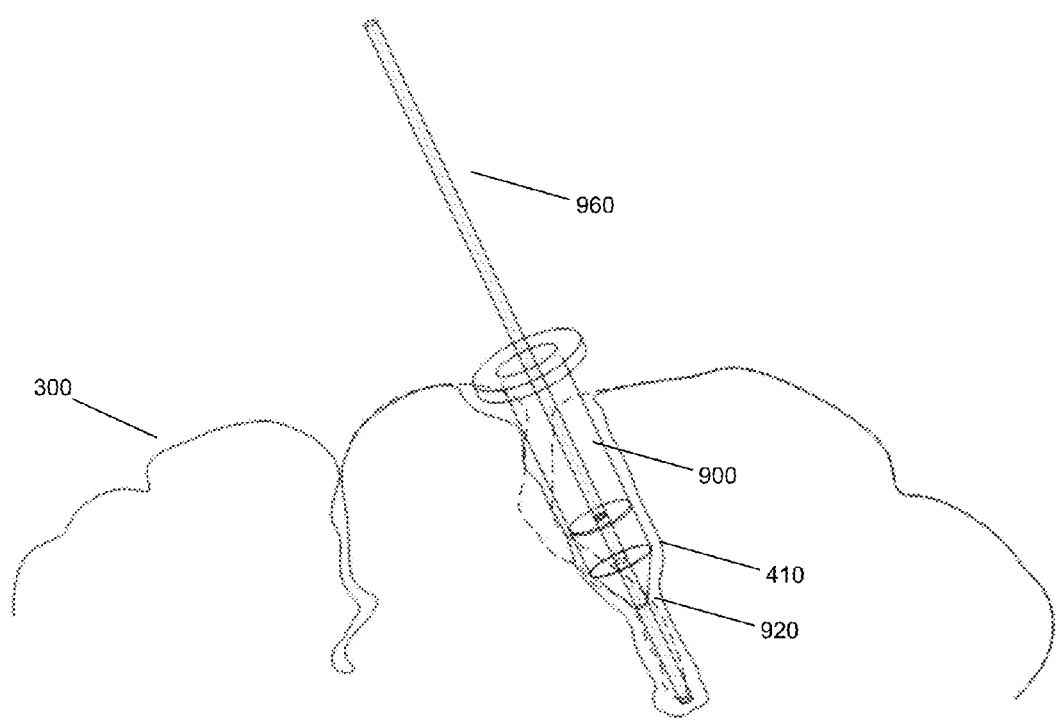
FIGS. 9B and 9C illustrates an example of a port with an adaptive tip inserted down a sulci path.

FIG. 9B is an exemplary embodiment illustrating an access port with an adaptive atraumatic tip inserted down a sulci path. In FIG. 9B, access port 900, is inserted down sulci path 410 of brain tissue 300. Access port 900 has an atraumatic tip 920 in a collapsed position. Probe 960 may also be placed down access port 900 to traverse the sulci path 410.

Figure 9C:
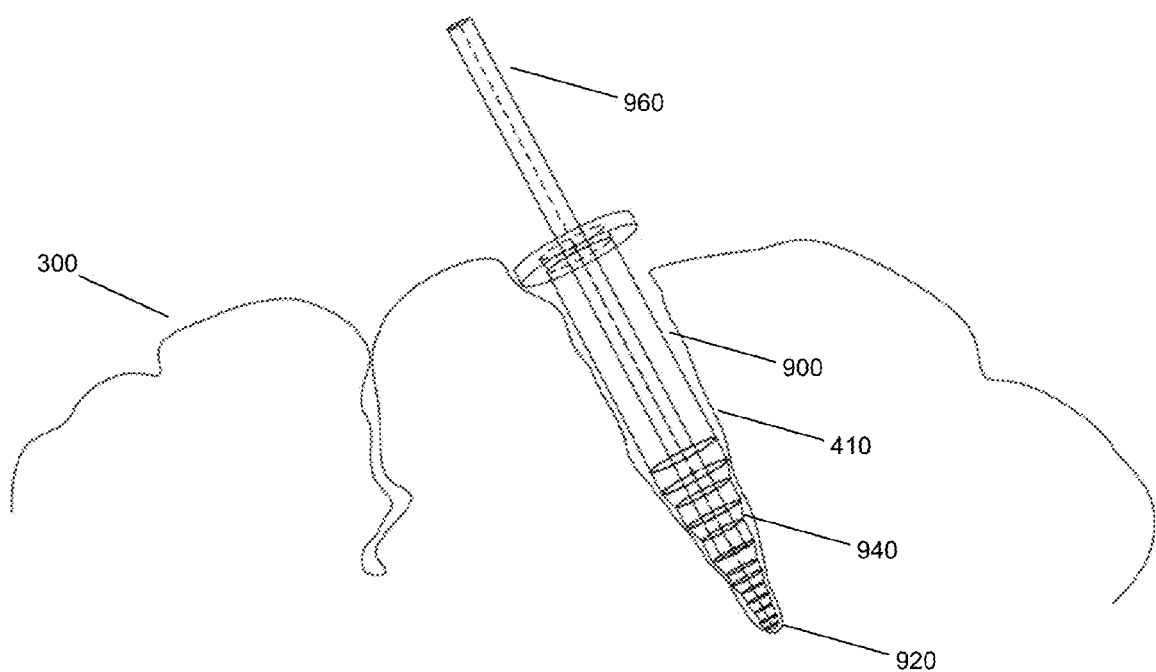

The atraumatic tip 920 of access port 900, or more generally the introducer or obturator, is able to adapt in its properties as it is inserted into the body. FIG. 9C is an exemplary embodiment illustrating an access port 900 with an atraumatic tip 920 in an extended position. In FIG. 9C, access port 900, is inserted down sulci path 410 of brain tissue 300. Access port 900 has a longer atraumatic tip 920 than the collapsed position illustrated in FIG. 9B. Extended concentric rings 940 form the longer atraumatic tip 920 in the deployed extended configuration. Probe 960 is also shown to traverse down access port 900 and through the extended concentric rings 940 to the desired target.

Figure 9D:
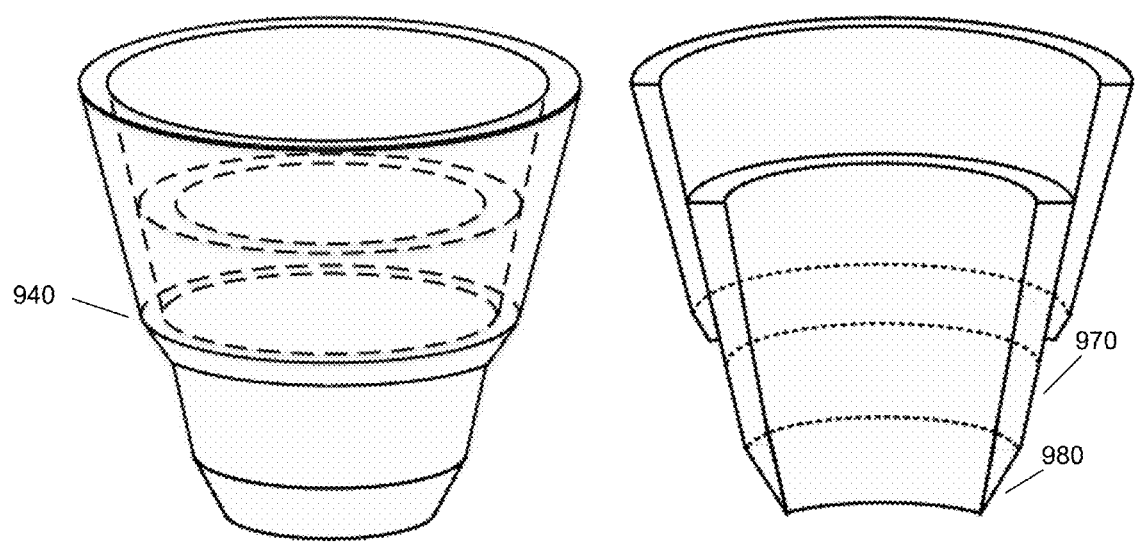
FIG. 9D illustrates an example of a sharp concentric ring of an adaptive tip.

The adaptive tip mechanism shown as atraumatic tip 920 may be further adapted from a blunt to a sharp configuration. A blunt configuration is suitable for penetrating softer tissue while a sharp configuration may be used to penetrate stiffer portions of the tissue. As illustrated in FIG. 9D, a sharp configuration may be provided by a sharp concentric ring 970 with a sharp distal edge 980 arranged as the most distally extended of the concentric rings 940.

In a preferred embodiment, the atraumatic tip may use strain gauges to provide feedback in order to measure shear strength. In other embodiments, strain and stress sensors may be placed on the outside of the cylindrical barrel 820 of the access port 800, so measurements can be taken as the access port is inserted into the brain 300. This information provides feedback as the access port is inserted, which can be used to minimize stress/strain on critical structures. Sensors can also provide functional information (i.e., electrical pulses from the nerve fibres, or blood flow from vessels) from the tissues adjacent to the access port or adaptive tip. Furthermore, an access port and/or adaptive tip provided with sensors can utilize the measurements taken by the sensors to direct the access port along the least invasive pathway into the brain toward the target tissue, In instances where an adaptive tip is extended into tissue, the adaptive tip can use the sensor or imaging information to direct its pathway.

The adaptive tip mechanism may be expanded in further embodiments to address multiple stages of insertion to traverse to a tumor location. These stages include:

1) Sulcus engagement—During sulcus engagement, the distal end of the adaptive tip is similar to the tip of the port, that is, not too sharp to cut through grey matter, but sharp enough to separate the gyri. Imaging can be used to view the overall sulci structure or, when the sulcus is engorged, where the entrance to the sulcus is.

2) Sulci insertion—Once in the sulci, the tip can be more blunt. The blunt tip reduces the chance of puncturing through the adjacent gyrus. At this stage, imaging to envision the sulci and the blood vessels at a larger scale is important.

3) Bottom of sulci engagement—After traversing sulci, the adaptive tip needs to puncture through the base of a sulcus. Here having a very high resolution image of the anatomy is important. For instance a high resolution ultrasound, or OCT image, or polarized light OCT (to view nerves) is valuable to locate the optimal incision site while avoiding nerves or vessels. Optimally a small controlled incision point should be made, based on imaging or based on sensor information. The incision may be made manually by inserting an instrument through a small orifice in the end of the introducer or by removing one of the introduced components in the introducer (multiple lumen)—to introduce a specific cutting tip.

To embody this, a variable tip access port—particularly one that can have a different angle of engagement, or openings to allow for small dilation devices, or cutting tools is envisioned.

4) Traversing the white matter—In order to traverse the white matter,—a particular cutting tip can be used, depending on tissue stiffness or where the adaptive tip is situated relative to major nerve bundles. A sharp tip can be used to make incisions through tissue, or a blunt tip can be used to separate natural separation points in the tissue, such as nerve fibers.

5) Puncture of the tumor—Depending on how well defined the edge of the tumor is, an appropriate tip can be selected to cut through the surface of the surrounding tissue, a suction device can be used to immobilize the tissue, or a blunt tip can be used to immobilize the tumor by encircling it. When the probe is close to the tumor, the appropriate device can be selected and used.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A surgical access port for navigating down a sulcal path of a neurosurgical procedure comprising:
    a. a cylindrical body having a proximal end and a distal end; and
    b. a guiding mechanism with an adaptive atraumatic tip for navigating down the sulcal path on a distal end of the access port;
    wherein the adaptive atraumatic tip comprises a plurality of collapsible rigid concentric rings, each concentric ring having a proximal edge closest to the access port and a distal edge furthest from the access port and wherein a distal ring has a smaller outer diameter than a proximal ring such that the plurality of concentric rings provides a conical shape in an extended configuration; wherein one or more of the plurality of concentric rings has a sharp distal edge to penetrate tissue.

2. The surgical access port as in claim 1, wherein the access port is attached to a high frequency vibration source.

3. The surgical access port as in claim 2, wherein the high frequency vibration source is a collar located around the body of the access port.

4. The surgical access port as in claim 2, wherein the vibration source comprises a driver, circuit, amplifier, oscillator and power supply.

5. The surgical access port as in claim 2, wherein a frequency and amplitude of the vibration source are activatable by a user.

6. The surgical access port as in claim 1, wherein the access port outer surface is coated with a low-friction coating.

7. The surgical access port as in claim 1, wherein one or more inflatable balloons are attached to the outer surface of the access port.

8. The surgical access port as in claim 1, wherein the access port has attached one or more sensors for guiding the surgical access port using a navigation system.

9. The surgical access port as in claim 8, wherein the one or more sensors are selected from a list comprising of an ultrasound, optical coherence tomography, fiber optics, light guides, Raman, PET, MRI, vibration, optical, strain or stress sensors.

10. The surgical access port as in claim 1, wherein the concentric rings are joined by a flexible membrane.

11. The surgical access port as in claim 10, wherein the flexible membrane includes a living hinge.

12. The surgical access port as in claim 10, wherein the flexible membrane is constructed of medical grade silicone.

13. The surgical access port as in claim 1, wherein the atraumatic tip has attached strain gauges to measure shear strength.

14. The surgical access port as in claim 1, wherein the atraumatic tip has attached strain and stress sensors.

15. The surgical access port as in claim 14, wherein the strain and stress sensors are used to guide the atraumatic tip using a navigation system.

16. A surgical access port for navigating down a sulcal path of a neurosurgical procedure comprising:
    a cylindrical body; and
    a guiding mechanism with an adaptive atraumatic tip for navigating down the sulcal path attached to the cylindrical body;
    wherein the adaptive atraumatic tip comprises a plurality of collapsible rigid concentric rings and a distal ring has a smaller outer diameter than a proximal ring such that the plurality of concentric rings provides a conical shape in an extended configuration; wherein one or more of the plurality of concentric rings has a sharp distal edge to penetrate tissue.

17. The surgical access port as in claim 16, wherein the access port has attached one or more sensors for guiding the surgical access port using a navigation system.

18. The surgical access port as in claim 17, wherein the one or more sensors are selected from a list comprising of an ultrasound, optical coherence tomography, fiber optics, light guides, Raman, PET, MRI, vibration, optical, strain or stress sensors.

19. The surgical access port as in claim 16, wherein the concentric rings are joined by a flexible membrane.

20. The surgical access port as in claim 16, wherein the atraumatic tip has attached strain gauges to measure shear strength.

21. The surgical access port as in claim 16, wherein the atraumatic tip has attached strain and stress sensors.

\* \* \* \* \*